United States Patent [19]

Arosio et al.

[11] Patent Number: 5,508,453
[45] Date of Patent: Apr. 16, 1996

[54] INTERMEDIATE FOR USE IN THE PREPARATION OF TAUROCHOLANIC ACIDS

[75] Inventors: Roberto Arosio, Civate; Vittorio Rossetti, Milan, both of Italy

[73] Assignee: Sanofi, Paris, France

[21] Appl. No.: 246,148

[22] Filed: May 19, 1994

[30]       Foreign Application Priority Data

May 20, 1993 [IT] Italy ................... TO93A0346

[51] Int. Cl.$^6$ ........................................ C07J 9/00
[52] U.S. Cl. .................. 552/553; 552/554; 552/555
[58] Field of Search ........................... 552/553, 554, 552/555, 556

[56]                References Cited

U.S. PATENT DOCUMENTS 4,088,760  5/1978  Benson et al. .
5,352,682  10/1994  Sipos ............................. 514/182

FOREIGN PATENT DOCUMENTS 0135782  4/1985  European Pat. Off. .
0400695  12/1989  European Pat. Off. .
3736918A1  5/1989  Germany .

OTHER PUBLICATIONS

Morrison & Boyd, *Organic Chemistry*, 4th ed. (1983) pp. 923–926 & 823–825.
J. Falbe, "Methoden der Organischem Chemie ...," 1985, Georg Thieme Verlag, Stuttgart, Germany, pp. 635–636 and 978–981, (no translation).

*Primary Examiner*—Kimberly J. Kestler
*Attorney, Agent, or Firm*—Bacon & Thomas

[57]                ABSTRACT

The present invention relates to intermediates for use in the preparation of taurocholanic acids. The intermediates have the following formula (IV):

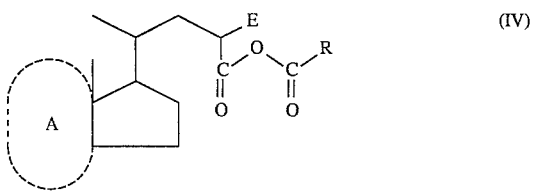

in which A completes the 5β-cyclopentaneperhydrophenanthrene structure of a cholanic acid; E is hydrogen or a methyl; and R is a hydrocarbon residue bonded to the carbonyl group by a tertiary carbon.

6 Claims, No Drawings

INTERMEDIATE FOR USE IN THE PREPARATION OF TAUROCHOLANIC ACIDS

The present invention relates to a process for the preparation of derivatives of cholanic acids conjugated with taurine, hereafter called taurochoianic acids, of formula (I):

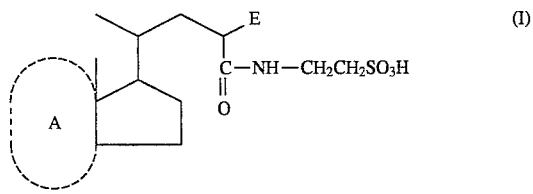

in which A completes the 5β-cyclopentaneperhydrophenanthrene structure of a cholanic acid and E is hydrogen or a methyl, and their pharmaceutically acceptable salts.

According to the present invention, the term "cholanic acids" includes unsubstituted or substituted cholanic acid itself (or 5β-cholan-24-oic acid) and the products resulting from its oxidation on the cyclopentaneperhydrophenanthrene structure, for example the derivatives with dihydroxy and trihydroxy on said structure, especially ursodeoxycholic acid (3α,7β-dihydroxy), chenodeoxycholic acid (3α,7α-dihydroxy), hyodeoxycholic acid (3α,6α-dihydroxy), deoxycholic acid (3α-hydroxy), cholic acid (3α,7α,12α-trihydroxy), ursocholic acid (3α,7β,12α-trihydroxy) and hyocholic acid (3α,6α,12α-trihydroxy).

Taurocholic acids, especially tauroursodeoxycholic acid and taurochenodeoxycholic acid, are compounds present in the organism which are stored in the gallbladder and which, when secreted with the bile, participate in the intestinal absorption of fats.

Ursodeoxycholic acid is used in therapy for the treatment of various degenerative conditions of the bile function, especially in the dysfunctions due to bile supersaturated with cholesterol, for dissolving the calculus in the gallbladder or for preventing its formation.

Some chemical syntheses of taurocholanic acids, more particularly tauroursodeoxycholic acid (TUDCA) and 23-methyltauroursodeoxycholic acid (23-TMUDCA), have been described in the literature.

Italian patent 1167038, for example, describes the preparation of tauroursodeoxycholic acid by the direct condensation of ursodeoxycholic acid and taurine in the presence of a condensation agent.

Italian patent 1197331 describes the preparation of tauroursodeoxycholic acid using the azide of ursodeoxycholic acid as a reaction intermediate.

European patent 135782 describes 23-methylcholanic acid derivatives and more particularly the preparation of 23-TMUDCA.

The synthesis of taurocholanic acids which seems to be the most widely used at the present time is the one illustrated in Italian patent 1212092, which describes the preparation of ursodeoxycholic acid amides, including that of tauroursodeoxycholic acid, via a mixed anhydride prepared by reacting ursodeoxycholic acid with an alkyl or phenyl chloroformate, and by treating said mixed anhydride with taurine. This reaction is particularly difficult because the anhydride formed is an unstable compound which readily decomposes; furthermore, the chloroformates used are very volatile compounds which are well known as potent, notoriously toxic chemical reactants. The reaction conditions, especially the temperature, must therefore be carefully monitored. In any case, even if caution is exercised, the yields are not very satisfactory.

It has now been found that the reaction of a cholanic acid derivative with an appropriate acid chloride gives mixed anhydrides which are particularly suitable for the subsequent reaction with taurine.

Thus, according to one of its features, the present invention relates to a process for the preparation of a taurocholanic acid of formula (I):

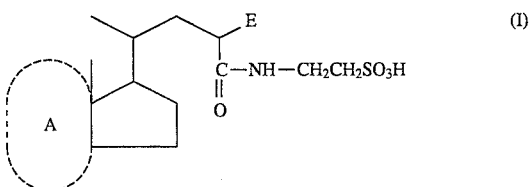

in which A and E are as defined above, or one of its salts, which comprises (a) treating a cholanic acid of formula (II):

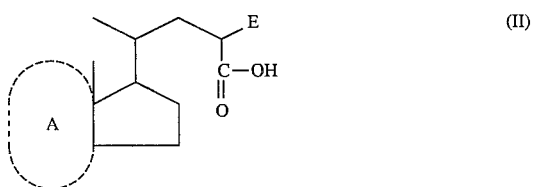

in which A and E are as defined above, with an acid chloride of formula (III):

in which R is a hydrocarbon residue bonded to the carbonyl group by a tertiary carbon, in the presence of a tertiary amine, optionally in a polar aprotic organic solvent which is miscible or partially miscible with water; and then (b) treating the resulting intermediate mixed anhydride of formula (IV):

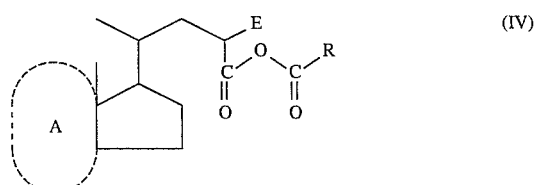

in which A, E and R are as defined above, with taurine and isolating the resulting product of formula (I), either as such or in the form of one of its salts.

If the final product is isolated in the form of a salt, this may or may not be pharmaceutically acceptable. In the latter case, the taurocholanic acid is isolated by neutralization of said salt and is optionally converted to another, pharmaceutically acceptable salt, preferably an alkali metal or alkaline earth metal salt.

According to a preferred feature, the process of the present invention produces tauroursodeoxycholic acid, 23-methyltauroursodeoxycholic acid, taurochenodeoxycholic acid and their pharmaceutically acceptable salts.

In step (a) of the process, the acid chloride of formula (III) is derived from a carboxylic acid of formula (III'):

in which R is a hydrocarbon residue bonded to the carbonyl by a tertiary carbon and preferably containing from 3 to 24 carbon atoms. The term "hydrocarbon" notably includes the saturated or unsaturated aliphatic or cycloaliphatic hydrocarbons and the aromatic hydrocarbons. More particularly, R can be a tertiary alkyl or alkenyl group such as propen-2-yl, tert-butyl, 2-methylbutyl (tert-pentyl) or triethylmethyl; an aromatic group such as a substituted or unsubstituted phenyl, for example phenyl or p-methylphenyl, a naphthyl, an anthracenyl, a phenanthrenyl, a 5,6,7,8-tetrahydronaphth-1-yl or a 5,6,7,8-tetrahydronaphth-2-yl; or a cycloaliphatic group such as cyclohex-1-enyl or 1-methylcyclohexyl; R is preferably tert-butyl or phenyl.

The acid chlorides of formula (III), which are sterically hindered, give mixed anhydrides which further virtually selective attachment of the taurine to the carbonyl group of the cholanic acid, resulting in a large increase in the final yield.

Examples of chlorides of formula (III) which can be used are pivaloyl chloride, benzoyl chloride, 2,2-dimethylvaleroyl chloride, 2-naphthoyl chloride, 1naphthoyl chloride, 1-methylcyclohexanecarboxylic acid chloride or cyclohex-1-enecarboxylic acid chloride, pivaloyl and benzoyl chlorides having proved particularly appropriate.

In general, the acid chloride of formula (III) is used in an equimolar amount or, preferably, in slight excess relative to the cholanic acid of formula (II).

The condensation reaction of step (a) is carried out in the presence of a tertiary amine which is preferably selected from those commonly used as Lewis bases, for example triethylamine, tributylamine, N-alkylpiperidines, especially N-methylpiperidine, pyridine or 4-dimethylaminopyridine.

It is customary to use an equimolar amount of such an amine relative to the starting acid, but it is possible to employ excess amine, for example if it is desired to carry out the reaction without using other solvents.

The reaction is preferably carried out in the presence of a polar or apolar, aprotic organic solvent which is miscible or partially miscible with water and which does not interfere with the course of the reaction. Examples of such solvents are dioxane, acetone and pyridine, either by themselves or in a mixture with one another.

The temperature is not a critical factor in the carrying-out of the reaction, it being possible for said temperature to be between 0° C. and 50° C., preferably between 10° C. and room temperature.

The reaction of step (a) starts immediately and finishes in a short time of at most a few hours. If desired, the reaction mixture can also be stirred for longer since the anhydride of formula (IV) formed is stable.

When step (a) is complete, any salts which have precipitated are filtered off and, if appropriate, the mixed anhydride is isolated. The next step, (b), involves reaction with taurine, either by direct addition of the latter to the reaction mixture, or by addition to a solution of the previously isolated mixed anhydride in an appropriate solvent.

In step (b), the taurine is used dissolved in a basic aqueous solution, but if the taurine is added to the reaction mixture obtained at the end of step (a) in which a large excess of tertiary amines has been used, the taurine as such can quite simply be added to said reaction mixture.

It is necessary to use at least an equimolar amount of taurine relative to the cholanic acid of formula (II); however, to ensure a better reaction yield, it is preferable to use an excess of taurine, advantageously of 30 to 40%.

The reaction mixture is preferably cooled slightly when the taurine is added. Once the addition is complete, the temperature is gradually allowed to rise, preferably being maintained between 10° C. and room temperature. In general, the reaction finishes in a few hours, taking the various reaction parameters into account, but the course of the reaction can in any case be monitored by the customary chromatographic techniques.

When the reaction is complete, any excess taurine which has not reacted is filtered off and discarded. The resulting taurocholanic acid of formula (I) is separated off and purified by the conventional methods. It usually suffices to add to the reaction mixture a solvent which forms an azeotrope with water, so that the reaction product precipitates; more rarely, the water has to be removed first by azeotropic distillation in order to induce precipitation.

Alternatively, once the reaction is complete and the excess taurine has been removed by filtration, an ion exchange resin can be used to improve the purification of the product. In this case, the solution is passed over two resins, firstly over a strongly acidic resin and then over a basic resin, and only after this double operation is the solvent added which permits separation of the final product.

If desired, the product obtained can subsequently be purified by crystallization from appropriate solvents.

The mixed anhydrides of formula (IV):

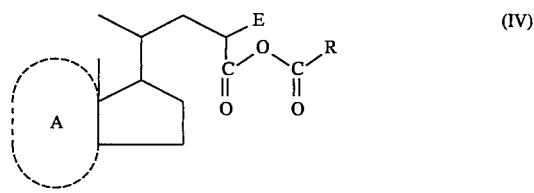

in which A, E and R are as defined above, are novel compounds and represent a further feature of the present invention. The anhydrides of formula (IV) in which A completes the structure of ursodeoxycholic acid or chenodeoxycholic acid and E and R are as defined above are particularly advantageous compounds; the mixed anhydrides of ursodeoxycholic acid, 23-methylursodeoxycholic acid and chenodeoxycholic acid with trimethylacetic acid or benzoic acid are particularly preferred.

If it is desired to isolate the anhydrides of formula (IV), the salts precipitated at the end of said step (a) are removed by filtration and the solution is evaporated under vacuum at a temperature not exceeding 30° C. to give the compounds (IV).

The following Examples illustrate the invention without however implying a limitation.

EXAMPLE 1

Tauroursodeoxycholic acid

Preparation 2.5 g (24.75 mmol) of triethylamine are added dropwise at a temperature of 20° C. to a suspension of 9.6 g (24.45 mmol) of ursodeoxycholic acid in 60 ml of dioxane. Once solubilized, the mixture is cooled to 10° C., 2.98 g (24.70 mmol) of pivaloyl chloride are added slowly and the temperature is then allowed to rise spontaneously to 20° C. The salts formed are filtered off and the precipitate is washed with dioxane, the washings being added to the solution. 3.84 g (30.72 mmol) of taurine dissolved in 24 ml of 1N NaOH are added to the solution obtained and the mixture is stirred for 3 hours at 15° C. The reaction can be followed by thin layer chromatography using $CHCl_3/MeOH/AcOH=70/30/5$ as the eluent.

Purification

1st METHOD

The unreacted taurine is removed by filtration; the solution is cooled to 0°–5° C. and 600 ml of acetone are added slowly. A sticky mass separates out and the solvent is removed by decantation. The residue is dissolved in 30 ml of water, 100 ml of toluene are added and the azeotrope is distilled to remove the water. This gives a solid, which is easily filtered off and washed with toluene.

2nd METHOD

The unreacted taurine is filtered off and the solution is passed over a 20 ml column of the cationic resin Rélite CF (acid form) and then over the resin Rélite GHl (free base) slowly. The solution is cooled to 0° C., 600 ml of acetone are added and the precipitate formed is filtered off and washed with acetone. M.p.: 135°–141° C.; IR (nujol) cm$^{-1}$: 1050 (—SO$_3$); 1545 and 1650 (amide); 1200 (—SO$_3$).

EXAMPLE 2

Tauroursodeoxycholic acid

The method of Example 1 is followed using 3.48 g (24.70 mmol) of benzoyl chloride instead of 2.98 g of pivaloyl chloride.

EXAMPLE 3

Taurochenodeoxycholic acid

Preparation

The method of Example 1 is followed using 9.6 g of chenodeoxycholic acid instead of ursodeoxycholic acid.

Purification

The excess taurine which has not reacted is removed by filtration, the filtrate is cooled to 0° C. and 600 ml of acetone are added slowly to the solution. The white solid which separates out is filtered off and washed with acetone. IR (nujol) cm$^{-1}$: 1050 (—SO$_3$); 1545 and 1650 ( amide ); 1200 (—SO$_3$).

EXAMPLE 4

Taurochenodeoxycholic acid

The method of Example 3 is followed using 3.48 g (24.70 mmol) of benzoyl chloride instead of pivaloyl chloride.

The characteristics of the products obtained by the reactions of Examples 1 to 4 are illustrated in Table I below.

TABLE I

| Example | Yield | Residual taurine | Residual starting acid |
| --- | --- | --- | --- |
| 1 | 77.4% | 1% | 1% |
| 2nd method of purification |  |  |  |
| 2 | 73.9% | 1% | 1% |
| 2nd method of purification |  |  |  |
| 3 | 75.4% | 1% | 2% |
| 4 | 60% | 0.5% | 0.5% |

EXAMPLE 5

Pivalic anhydride of tauroursodeoxycholic acid

The method of Example 1 is followed up to the filtration of the salts. The solvent is evaporated off under reduced pressure at a temperature not exceeding 30° C. The residue is dissolved in chloroform and extracted with water. The two phases are separated, the organic phase is dried over sodium sulfate and the solvent is evaporated off under reduced pressure at low temperature to give the trimethylacetic anhydride of 3α,7β-dihydroxy-5β-cholan-24-oic acid. IR (nujol) cm$^{-1}$: 1810, 1720.

The more significant data of the $^{13}$C NMR spectrum are collated in the Table below.

| ATOM N* | PPM |
| --- | --- |
| 1 | 28.52 |
| 2 | 29.88 |
| 3 | 168.78 |
| 4 | 173.37 |
| 5 | 35.05 |
| 6 | 24.92 |
| 7 | 24.92 |
| 8 | 24.92 |

EXAMPLE 6

Benzoic anhydride of tauroursodeoxycholic acid

The method of Example 5 is followed using 3.48 g (24.70 mmol) of benzoyl chloride instead of pivaloyl chloride. This gives the benzoic anhydride of 3α,7β-dihydroxy-5β-cholan-24-oic acid.

The more significant data of the $^{13}$C NMR spectrum are collated in the Table below.

| ATOM N* | PPM |
| --- | --- |
| 1 | 28.52 |
| 2 | 29.88 |
| 3 | 168.76 |
| 4 | 161.66 |
| 5 | 129.39 |
| 6 | 130.57 |
| 7 | 128.84 |
| 8 | 131.89 |
| 9 | 128.84 |
| 10 | 130.57 |

What is claimed is:
1. An anhydride of formula (IV):

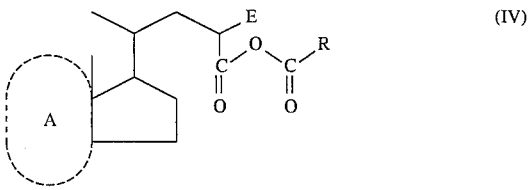

in which A completes the 5β-cyclopentaneperhydrophenanthrene structure of a cholanic acid, E is hydrogen or a methyl and R is a hydrocarbon residue bonded to the carbonyl group by a tertiary carbon.

2. An anhydride according to claim 1 wherein R is a hydrocarbon residue bonded to the carbonyl by a tertiary carbon and containing from 3 to 24 carbon atoms.

3. An anhydride according to claim 1 wherein A completes the structure of ursodeoxycholic acid and R is a tert-butyl or phenyl group.

4. An anhydride according to claim 1 wherein A completes the structure of chenodeoxycholic acid and R is a tert-butyl or phenyl group.

5. The benzoic anhydride of 3α,7β-dihydroxy-5β-cholan-24-oic acid.

6. The trimethylacetic anhydride of 3α,7β-dihydroxy-5β-cholan-24-oic acid.

* * * * *